United States Patent [19]

Tolstikov et al.

[11] 4,270,016
[45] May 26, 1981

[54] METHOD OF PREPARING TRANS-, TRANS-, TRANS-1,5,9-CYCLODODECATRIENE

[76] Inventors: Genrikh A. Tolstikov, ulitsa Pushkina, 54, kv. 49; Usein M. Dzhemilev, ulitsa Dostoevskogo, 102/3, kv. 61, both of Ufa; Grigory I. Rutman, ulitsa Revoljutsionnaya, 7, kv. 6, Sterlitamak; Jury I. Michurov, prospekt Lenina, 13, kv. 4, Sterlitamak; Boris I. Pantukh, ulitsa Khudaiberdina, 162, kv. 89, Sterlitamak; Stanislav S. Shavanov, ulitsa Mira, 59, kv. 29, Sterlitamak; Sagid R. Rafikov, ulitsa Novaya Mostovaya, 25, kv. 9, Ufa; Sofia A. Egoricheva, ulitsa Nugumanova, 66a, kv. 23, Sterlitamak; Valery P. Juriev, ulitsa Dostoevskogo, 102/3, kv. 14, Ufa; Alexandr G. Liakumovich, ulitsa Galeeva, 10, kv. 8, Kazan; Valerian M. Sobolev, naberezhnaya M. Gorkogo, 46/50, kv. 185, Moscow; Boris S. Korotkevich, ulitsa Fortunatovskaya, 31/35, kv. 71, Moscow; Jury A. Shmuk, Leninsky prospekt, 13, kv. 31, Moscow; Elena Y. Mandelshtamm, prospekt Mira, 72, kv. 2, Moscow, all of U.S.S.R.

[21] Appl. No.: 44,778

[22] Filed: Jun. 1, 1979

[51] Int. Cl.³ .................. C07C 2/42; C07C 13/02
[52] U.S. Cl. ...................... 585/366; 585/369; 585/370
[58] Field of Search ............ 585/23, 366, 369, 370

[56] References Cited
U.S. PATENT DOCUMENTS 3,247,270  4/1966  Kirk ..................... 585/369
3,390,195  6/1968  Chappell et al. .......... 585/370

FOREIGN PATENT DOCUMENTS 1105589  3/1968  United Kingdom ........... 585/366

Primary Examiner—Veronica O'Keefe
Attorney, Agent, or Firm—Haseltine and Lake

[57] ABSTRACT

A method of preparing trans-, trans-, trans-1,5,9-cyclododecatriene which comprises cyclotrimerization of butadiene at a temperature within the range of from 50° to 150° C. in the presence of a catalytic system consisting of a compound of bivalent nickel, an organo-aluminium compound of the formula (1) or (2):

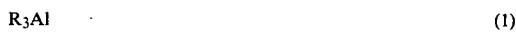

(1)

and

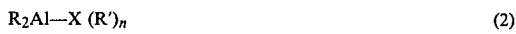 (2)

wherein R, and R' are each $C_2H_5-$,

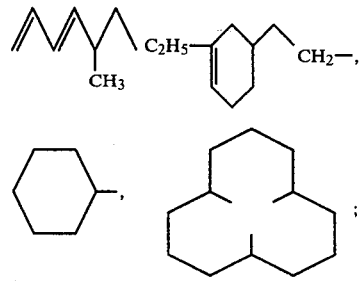

X is $-O-$ when $n=1$ and $-N-$ when $n=2$; and an activator, viz. a compound of formula (3) or (4):

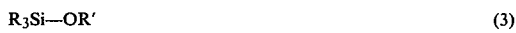

(3)

wherein R is an alkyl; R' is an alkyl, $C_6H_5-$, $C_6H_{11}$,

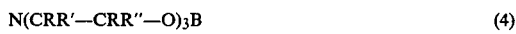 (4)

wherein R and R'' are each $CH_3-$, $C_2H_5-$, $C_6H_{10}$, $C_8H_{11}-$, $H-$; R is $H-$.

The method according to the present invention makes it possible to increase the yield of the desired product up to 95% by weight.

3 Claims, No Drawings

METHOD OF PREPARING TRANS-, TRANS-, TRANS-1,5,9-CYCLODODECATRIENE

FIELD OF THE INVENTION

The present invention relates to the art of petrochemical synthesis and, more specifically, to a method of preparing trans-,trans-,trans-1,5,9-cyclododecatriene which is useful in commercial organic synthesis for the preparation of dodecanedicarboxylic acid, laurinolactam, macrocyclic alcohols, ketones and other valuable products.

BACKGROUND OF THE INVENTION

Known in the art is a method of preparing trans-,trans-,trans-1,5,9-cyclododecatriene by way of cyclotrimerization of butadiene at a temperature within the range of from 50° to 200° C. in the presence of a homogeneous catalyst including a compound of a bivalent nickel such as nickel acetylacetonate, and an organo-aluminium reducing agent such as $(C_2H_5)_2AlOC_2H_5$ in a medium of an organic solvent.

The process occurs according to the following scheme:

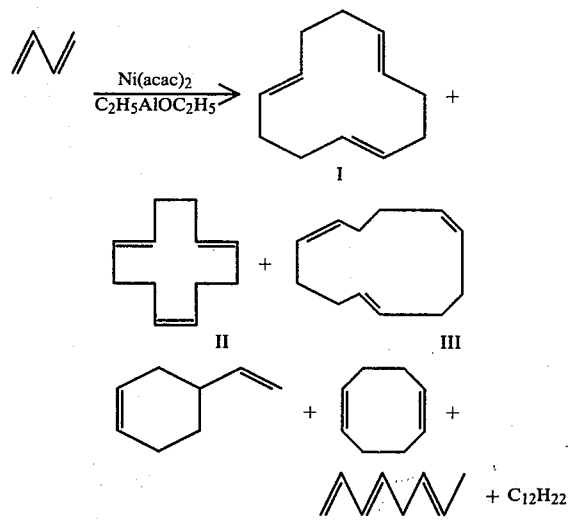

The yield of the desired product is as high as 75% by weight. Optimal temperature of the process is within the range of from 110° to 120° C.

This method, however, features a low selectivity and an insufficient yield of the desired product. Low selectivity of the process is revealed in the formation of cyclodimers of butadiene and its linear dimers and trimers. Furthermore, cyclotrimers are represented by a mixture of geometric isomers of trans-,trans-,trans- (I), trans-,trans-,cis- (II) and trans-,cis-,cis-cyclododecatrienes (III).

Also known in the art is a method of preparing trans-,trans-,trans-1,5,9-cyclododecatriene which comprises cyclotrimerization of butadiene at a temperature of 50° to 250° C. in the presence of a homogeneous catalyst containing a compound of bivalent nickel, an organo-aluminium compound and an activator in a medium of an organic solvent. As the activator use is made of pyridine. Addition of pyridine to the catalyst makes it possible to increase selectivity of the latter and, hence, increase selectivity of the process.

However, the yield of the desired product is 78% at the process duration of 12 hours at a temperature of from 110° to 120° C. Disadvantages of this prior art process also reside in a low yield of the desired product, long duration of the technological process. An essential disadvantage of the above-mentioned prior art methods resides in the use of hazardous organo-aluminium reducing agents.

SUMMARY OF THE INVENTION

It is the main object of the present invention to increase the process selectivity and increase the yield of the desired product.

One of important objects of the present invention is to simplify the process technology.

This object is accomplished by that in a method of preparing trans-,trans-,trans-1,5,9-cyclododecatriene by way of cyclotrimerization of butadiene at a temperature of from 50° to 150° C. in the presence of a catalytic system consisting of a compound of bivalent nickel, an organo-aluminium compound, an activator, in a medium of an organic solvent, in accordance with the present invention, use is made of the organo-aluminium compound of formula (I) or (2)

$$R_3Al \quad (1)$$

$$R_2Al-X(R')_n$$

wherein: R and R' are each $C_2H_5-$,

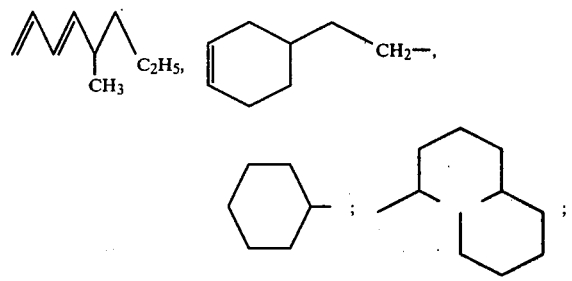

X is $-O-$ when $n=1$; $-N-$ when $n=2$;
as the activator use is made of a compound of formula (3) or (4):

$$R_3Si-OR' \quad (3)$$

wherein R is an alkyl; R' is an alkyl, $C_6H_5-$, $C_6H_{11}-$;

$$N(CRR'-CRR''-O)_3B \quad (4)$$

wherein R' and R" are each $CH_3-$, $C_2H_5-$, $C_6H_{10}-$, $C_8H_{11}-H-$; R is $H-$.

Incorporation of the above-indicated activator into a homogeneous catalytic system contributes to a substantial increase of the catalyst selectivity and efficiency. The combined use of said organo-aluminium compound and said activator in the catalytic system makes it possible to carry out the process of cyclotrimerization of butadiene under rather mild conditions (temperature of 80°-90° C.) while retaining a high yield of the desired product.

It is advisable, with the view to increase the yield of the desired product, to use the catalyst at a molar ratio of the compound of bivalent nickel to the activator and the organo-aluminium compound of 1:1-2:3-10 respectively.

It is preferable to use nickel acetylacetonate and nickel naphthenate as the compound of bivalent nickel.

DETAILED DESCRIPTION OF THE INVENTION

The method of preparing trans-,trans-,trans-1,5,9-cyclododecatriene according to the present invention is preferably embodied in the following manner.

A homogeneous catalytic system is preliminary prepared. To a solution of a compound of bivalent nickel, for example nickel acetylacetonate, in an organic solvent such as toluene at the temperature of 0° C. in a current of argon there is added an organo-aluminium reducing agent and the mixture is stirred for one hour. Then the resulting catalytic solution is added, under stirring, with an organo-silicon or organo-boron activator and the mixture is stirred for additional 0.5 hour.

Into an autoclave, in a current of argon, there are successively charged a solution of the above-specified catalyst and a solution of butadiene. The reaction mixture is heated at the temperature of 90° C. for three hours. The autoclave is cooled, its contents is discharged therefrom, washed with a 5% solution of HCl to the neutral reaction, dried over $MgSO_4$ and distilled in vacuum.

The yield of trans-,trans-,trans-1,5,9-cyclododecatriene is equal to 95–99% by weight.

The organo-aluminium reducing agent comprises a compound of formula (I) or (2)

$R_3Al$                                                              (1)

$R_2Al—X(R')_n$                                (2)

wherein: R and R' are each $C_2H_5$—,

, 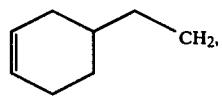

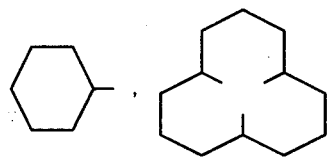

X is —O— at n=1; —N— at n=2.

This organo-aluminium reducing agent comprises a liquid which is inert relative to air and water, wherefore it it is not hazardous. This simplifies the technological process of the preparation of the desired product and ensures its safety.

As the activator, into the catalytic system there is added an ester of boric acid with a derivative of triethanolamine of the formula (4):

$N(CRR'—CRR''—O_3)B$ wherein R' and R'' are $CH_3$—, $C_2H_5$—, $C_6H_{10}$—, $C_8H_{11}$—, H—; R is H—,
or a siloxane ester of the formula (3):

$R_3Si—OR'$ wherein R is an alkyl; R' is an alkyl, $C_6H_5$—, $C_6H_{11}$.

Incorporation of said activator, i.e. siloxane ester or boric acid ester into the composition of the composition of the catalytic system makes it possible to increase activity and selectivity of the latter. This positive effect is achieved through coordination of said activator with nickel ion with the formation of sufficiently stable intermediately active complexes of nickel which take part in the process of cyclotrimerization of butadiene.

The combination of the above-specified organo-aluminium compound containing cycloalkyl, alkenyl radicals as well as hetero atoms (O, N) in its molecule with a readily available and inexpensive siloxane ester or boric acid ester makes it possible to produce a most active, stable and selectively-functioning catalytic system for the process of cyclo-trimerization of butadiene to individual trans-,trans-,trans-1,5,9-cyclododecatriene.

The method according to the present invention has the following advantages over the prior art methods:
- a high selectivity with respect to trans-,trans-,trans-1,5,9-cyclododecatriene;
- a high yield of the desired product (about 98%);
- simplified process technology owing to lowered temperature, reduced duration and use of a non-hazardous organo-aluminium reducing agent.

EXAMPLE 1

A catalyst is preliminary prepared following the procedure described hereinbelow.

To a solution of 0.02 mole of nickel acetylacetonate $Ni(acac)_2$ in 60 ml of toluene at the temperature of 0° C. in a current of argon there is added 0.2 mole of

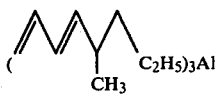

and stirred for one hour. Then the catalytic solution is added with 0.04 mole of $N(CNC_6H_{10}—CHC_6H_{10}—O)_3B$ and stirring is continues for additional 0.5 hour.

Into a 2 l autoclave, in a current of argon, there are successively added a solution of the catalyst prepared as described hereinabove and 1,000 g of butadiene. The three reaction mixture is heated at the temperature of 90° C. for three hours. The autoclave is cooled, the content thereof is discharged, the catalyst is decomposed with 20 ml of methanol, washed with a 5% solution of hydrochloric acid and with water to the neutral reaction, dried over $MgSO_4$ and distilled in vacuum.

The desired product, i.e. trans-,trans-,trans-1,5,9-cyclododecatriene isolated by distillation in vacuum has the following constants:

Boiling point 96° C. under 10 mm Hg (melting point is 34° C.);

IR spectrum ($v$, cm$^{-1}$); 975; 3,030 (trans —CH=CH—); PMR—spectrum: ($\delta$, m.g.) 1.5–1.9 (12 H, —CH$_2$—); 5.1–5.2 (6H—CH=CH—), m/1 162.

cis-cis-1,5-cyclo-octadiene; Boiling point 149°–150° C.; $n_D^{20}$ 1.5078 (Boiling point/from literature/14-9°–150° C.; $n_D^{20}$=1.5065;

4-vinylcyclohexene: Boiling point 128°–129° C., $n_D^{20}$=1,4640 (according to literature: Boiling point 128°–129° C.; $n_D^{20}$=1.4640).

The yield of trans-,trans-,trans-1,5,9-cyclododecatriene is 98% by weight.

It should be noted that in addition to trans-,trans-,trans-1,5,9-cyclododecatriene there is formed a mixture of isomeric trans-,trans-,cis-1,5,9-cyclododecatriene and trans-,cis-,cis-1,5,9-cyclododecatriene; the total yield thereof doe not exceed 1.5-2% by weight.

EXAMPLE 2

Cyclotrimerization of 1 kg of butadiene is performed using a catalytic system consisting of 0.02 mole of Ni(acac)$_2$ 0.02 mole of N(CH$_2$—CH$_2$—O)$_3$B and 0.2 mole of

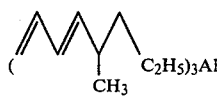

under conditions similar to those described in the foregoing Example 1. The yield of trans-,trans-,trans-1,5,9-cyclododecatriene is 975 g (97.5% by weight).

EXAMPLE 3

Cyclotrimerization of 1 kg of butadiene is performed using a catalytic system consisting of 0.01 mole of Ni(acac)$_2$ 0.02 mole of N(CHCH$_3$—CHCH$_3$—O)$_3$B and 0.1 mole of

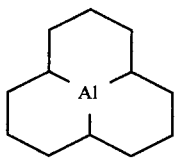

under the conditions of Example 1 hereinbefore.

The yield of trans-,trans-,trans-1,5,9-cyclododecatriene is 980 g (98% by weight).

EXAMPLE 4

Cyclotrimerization of 1 kg of butadiene is performed using a catalytic system consisting of 0.02 mole of Ni(acac)$_2$, 0.02 mole of N(CH$_2$—CH$_2$—O)$_3$B and 0.1 mole of (C$_6$H$_{11}$)$_2$Al—N(C$_2$H$_5$)$_2$ under conditions similar to those described in the foregoing Example 1. The yield of a mixture of hydrocarbons is 965 g, wherefrom 95% by weight constitutes trans-,trans-,trans-1,5,9-cyclododecatriene and 5% by weight 4-vinylcyclohexene.

EXAMPLE 5

Cyclotrimerization of 1 kg of butadiene under the conditions described in Example 1 hereinbefore using a catalytic system consisting of 0.02 mole of No(acac)$_2$, 0.04 mole of N(CHCH$_3$—CH$_2$—O)$_3$B and 0.02 mole of

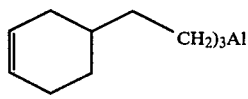

results in the preparation of 980 g of trans-,trans-,trans-1,5,9-cyclododecatriene.

EXAMPLE 6

Cyclotrimerization of 1 kg of butadiene is performed using a catalytic system consisting of 0.02 mole of Ni(acac)$_2$ 0.02 mole of N(CHCH$_3$—CH$_2$—O)$_3$B and 0.2 mole of

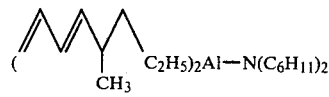

under the conditions similar to those described in Example 1. The yield of trans-,trans-,trans-1,5,9-cyclododecatriene is 976 g.

EXAMPLE 7

Cyclotrimerization of 0.5 kg of butadiene is conducted under conditions similar to those of Example 1 hereinbefore in the presence of a catalytic system consisting of 0.01 mole of Ni(acac)$_2$, 0.01 mole of N(CH$_2$CHC$_2$H$_5$—O)$_3$B and 0.03 mole of

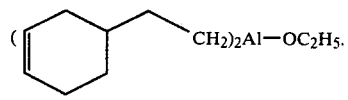

The yield of trans-,trans-,trans-1,5,9-cyclododecatriene is 95% by weight.

EXAMPLE 8

Cyclotrimerization of 1 kg of butadiene is conducted using a catalytic system consisting of 0.02 mole of Ni(acac)$_2$ 0.2 mole of

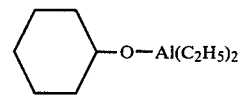

and 0.02 mole of N(CHC$_2$H$_5$—CHC$_2$H$_5$—O)$_3$B under the conditions described in Example 1. The yield of a mixture of cyclic isomers of 1,5,9-cyclododecatrienes is 890 g, wherefrom trans-,trans-,trans-1,5,9-cyclododecatriene constitutes 98% by weight.

EXAMPLE 9

Cyclotrimerization of 1 kg of butadiene on a catalytic system consisting of 0.02 mole of Ni (acac)$_2$, 0.02 mole of N(CHR'—CHR'—O)$_3$B, wherein R' is C$_8$H$_{11}$— and 0.1 mole of

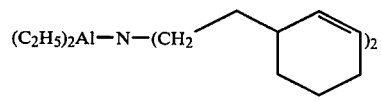

results in the preparation of 975 g of trans-,trans-,trans-1,5,9-cyclododecatriene containing at most 1.5% of isomeric trans-,trans-,cis- and trans-,cis-,cis-1,5,9cyclododecatrienes.

EXAMPLE 10

To a catalytic system prepared from 0.02 mole of nickel naphthenate, 0.2 mole of

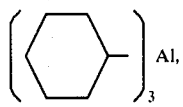

0.04 mole of $(C_{10}H_{21})_3$ SiOCH$_3$ there are added 600 g of butadiene and the mixture is heated at the temperature of 90° C. for three hours. The yield of a mixture of cyclooligomers is 590 g, wherefrom 92% by weight is trans-,trans-,trans-1,5,9-cyclododecatriene, 4% by weight is cis-,cis-1,5-cyclooctadiene and 4% by weight is 4-vinylcyclohexene.

EXAMPLE 11

Cyclotrimerization of 600 g of butadiene on a catalyst consisting of 0.02 mole of Ni(acac)$_2$, 0.2 mole of $(CH_3)_3$-SiOC$_6$H$_5$, 0.05 mole of $(C_2H_5)_3$Al under the conditions described in the foregoing Example 1 gives 593 g of a mixture of cyclooligomers. This mixture contains 91% by weight of trans-,trans-,trans-1,5,9-cyclododecatriene, 5% by weight of cis-,cis-,1,5-cyclooctatriene and 4% by weight of 4-vinylcyclohexene.

EXAMPLE 12

Cyclotrimerization of 600 g of butadiene using a catalytic system consisting of 0.02 mole of nickel naphthenate, 0.04 mole of $(CH_3)_2Si$—$(OC_6H_5)_2$ and 0.02 mole of $(C_2H_5)_2$

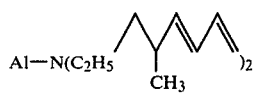

under the conditions described in the foregoing Example gives 580 g of cyclooligomers. The content of trans-,trans-,trans-1,5,9-cyclododecatriene is 90% by weight, cis-,cis-1,5-cyclooctadiene 5% by weight and 4-vinylcyclohexene 5% by weight.

EXAMPLE 13

Cyclotrimerization of 600 g of butadiene, under the conditions described in Example 1 hereinbefore, using a catalytic system consisting of 0.02 mole of Ni(acac)$_2$, 0.04 mole of $(CH_3)_3$—Si—OCH$_3$ and 0.06 mole of

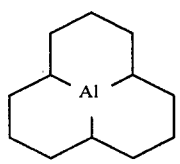

gives 585 g of a mixture of cyclo-oligomers containing 91% by weight of trans-,trans-,trans-1,5,9-cyclododecatriene, 4% by weigh of cis-,cis-1,5-cyclooctadiene, 5% by weight of 4-vinylcyclohexene.

EXAMPLE 14

Om a catalytic system consisting of 0.02 mole of Ni(acac)$_2$, 0.04 mole of $(CH_3)_3Si$—OC$_6$H$_{11}$ and 0.1 mole of

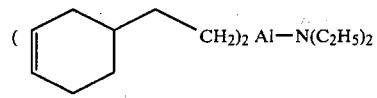

from 600 g of butadiene, under the conditions similar to those described in the foregoing Example 1, there are prepared 595 g of cyclo-oligomers. The resulting mixture of the oligomers contains 95% by weight of trans-,trans-,trans-1,5,9-cyclododecatriene, 4% by weight of cis-,cis-1,5-cyclooctadiene and 1% by weight of 4-vinylcyclohexene.

EXAMPLE 15

Cyclotrimerization of 300 g of butadiene on a catalytic-system consisting of 0.01 mole of Ni(acac)$_2$, 0.1 mole of

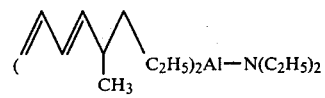

and 0.01 mole of $(CH_3)_3$—Si—OC$_7$H$_{15}$ under the conditions described in the foregoing Example 1 gives 265 g of a mixture of cyclo-oligomers consisting of 92% by weight of trans-,trans-,trans-1,5,9-cyclododecatriene, 6% by weight of cis-,cis-1,5-cyclooctadiene and 2% by weight of 4-vinylcyclohexene.

EXAMPLE 16

Cyclotrimerization of 600 g of butadiene on a catalytic system consisting of 0.02 mole of Ni(acac)$_2$, 0.02 mole of $(CH_3)_3Si)OC_{10}H_{21}$ and 0.1 mole of

conditions similar to those described in the foregoing Example 1 gives 580 g of a mixture of cyclo-oligomers containing 90% by weight of trans-,trans-,trans-1,5,9-cyclododecatriene, 7% by weight of cis-,cis-1,5-cyclooctadiene and 3% by weight of 4-vinylcyclohenexe.

EXAMPLE 17

Under the conditions similar to those of Example 1 cyclotrimerization of 600 g of butadiene on a catalytic system consisting of 0.02 mole of Ni(acac)$_2$, 0.02 mole of $(CH_3)_3Si$—OC$_{25}$H$_{51}$ and 0.1 mole of

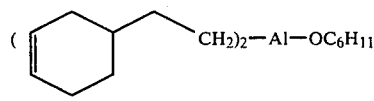

gives 580 g of a mixture of oligomers consisting of 92% by weight of trans-,trans-,trans-1,5,9-cyclododecatriene, 5% by weight of cis-,cis-1,5-cyclooctadiene and 3% by weight of 4-vinylcyclohexene.

EXAMPLE 18

Cyclotrimerization of 300 g of butadiene on a catalytic system consisting of 0.01 mole of nickel naphthenate, 0.01 mole of $(C_7H_{15})_3SiOC_{25}H_{51}$, 0.01 mole of

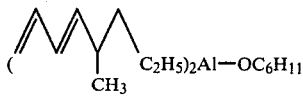 $(C_2H_5)_2Al-OC_6H_{11}$ under the conditions similar to those described in the foregoing Example 1 gives 580 g of a mixture of cyclo-oligomers consisting of 90% by weight of trans-,trans-,trans-1,5,9-cyclododecatriene, 4% by weight of cis-,cis-1,5-cyclooctadiene and 6% by weight of 4-vinylcyclohexene.

EXAMPLE 19

Cyclotrimerization of 600 g of butadiene using a catalytic system consisting of 0.02 mole of nickel naphthenate, 0.04 mole of $(C_{25}H_{51})_3Si-OC_6H_{11}$ and 0.06 mole of

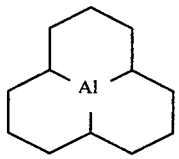

under the conditions similar to those described in Example 1 hereinbefore gives 580 g of a mixture of cyclooligomers consisting of 90% by weight of trans-,trans-,trans-1,5,9-cyclododecatriene, 7% by weight of cis-,cis-1,5-cyclooctadiene and 3% by weight of 4-vinylcyclohexene. The total yield of cyclo-oligomers is at least 95% by weight.

Trans-,trans-,trans-1,5,9-cyclododecatriene prepared in the foregoing Examples 2 through 19 has its constants similar to those described in Example 1 hereinbefore.

What is claimed is:

1. A method of preparing trans-,trans-,trans-1,5,9-cyclododecatriene comprising cyclotrimerization of butadiene at a temperature within the range of from 50° to 150° C. in the presence of a catalytic system consisting of a compound of bivalent nickel, an organo-aluminium compound selected from the group consisting of compounds of formula (I) or (2)

$$R_3Al \qquad (I)$$

$$R_2Al-X(R')_n \qquad (2)$$

wherein R and R' are selected from the group consisting of $C_2H_5-$,  $C_2H_5-$, 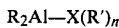

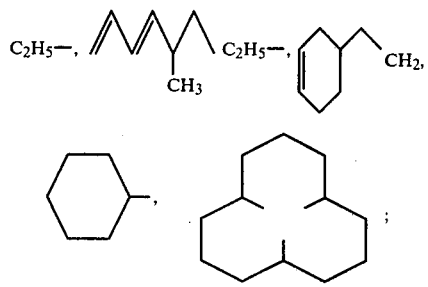

X is $-O-$ when $n=1$, $-N$ when $n=2$; and an activator, viz. a compound selected from the group consisting of compounds of formula (3) and (4);

$$R_3Si-OR' \qquad (3)$$

wherein R is an alkyl; R' is selected from the group consisting of $C_6H_5-$, $C_6H_{11}-$, an alkyl;

$$N(CRR'-CRR'')_3B \qquad (4)$$

wherein R' and R" are selected from the group consisting of $CH_3-$, $C_2H_5-$, $C_6H_{10}-$, $C_8H_{11}-$, $H-$; R is $H-$.

2. A method as claimed in claim 1, wherein said catalyst is used at a molar ratio between the compound of bivalent nickel, the activator and the organo-aluminium compound equal to 1:1–2:3–10 respectively.

3. A method as claimed in claim 1, wherein as the compound of bivalent nickel use is made of nickel acetalacetonate, nickel naphthenate.

* * * * *